United States Patent [19]
Burke

[11] Patent Number: 5,997,542
[45] Date of Patent: Dec. 7, 1999

[54] SURGICAL WIRE ASSEMBLY AND METHOD OF USE

[75] Inventor: Dennis W. Burke, Milton, Mass.

[73] Assignee: Biomet, Inc., Warsaw, Ind.

[21] Appl. No.: 08/972,866

[22] Filed: Nov. 18, 1997

[51] Int. Cl.⁶ .................................................. A61B 17/56
[52] U.S. Cl. ................................. 606/74; 606/61; 606/73
[58] Field of Search .................................. 606/61, 62, 73, 606/74, 103, 107, 139, 201, 202, 203, 113, 135, 141; 623/13, 15; 600/7, 434; 604/280; 24/170

[56] References Cited

U.S. PATENT DOCUMENTS

| | | | |
|---|---|---|---|
| 4,776,851 | 10/1988 | Burchman et al. | 623/13 |
| 5,536,270 | 7/1996 | Songer et al. | |

OTHER PUBLICATIONS

The Songer Cable System videotape, copyright 1991.
Cole Pelvic Cable (2mm), Cable assembly drawing dated Apr. 26, 1995 (believed to have been first sold by Biomet, Inc. on May 23, 1995).
Cole Pelvic Cable (2mm), Washer with sleeve drawings, dated Apr. 26, 1995 (believed to have been first sold by Biomet, Inc. on May 23, 1995).
Cole Pelvic Cable (2mm), 2mm needle drawing, dated Jan. 8, 1997 (believed to have been first sold by Biomet, Inc. on May 23, 1995).

*Primary Examiner*—Michael Buiz
*Assistant Examiner*—Lien Ngo
*Attorney, Agent, or Firm*—Harness, Dickey & Pierce, P.L.C.

[57] ABSTRACT

A surgical wire assembly comprises a first portion comprising a cable including multiple elongated strands of metal, and a second portion comprising an elongated solid strand of metal, the first and second portions being joined end-to-end. The first portion is more flexible than the second portion, and the second portion is provided with a tensile strength exceeding the tensile strength of the first portion. There is further disclosed a method for applying the surgical wire assembly to bone.

17 Claims, 4 Drawing Sheets

SURGICAL WIRE ASSEMBLY AND METHOD OF USE

FIELD OF THE INVENTION

This invention relates to medical apparatus and procedures in general, and more particularly to an improved surgical wire assembly and method of use.

BACKGROUND OF THE INVENTION

Surgical wire is used in many medical procedures for holding together bone.

For example, surgical wire may be used to hold together two or more pieces of the same bone, e.g., in the case of a fractured or surgically separated bone. Alternatively, surgical wire may be used to hold together two or more different bones, e.g., in the case of a surgical repair or reconstruction. Furthermore, surgical wire may also be used to reinforce a bone, e.g., in the case where a bone has been weakened by age or disease or injury.

In these and other situations, a length of surgical wire is generally wrapped around the bone which is to be held together, and then the two free ends of the wire are made fast to one another, e.g., by twisting together the two free ends of the surgical wire.

By way of example, in a so-called "total hip replacement" procedure, the top end of the patient's femur is replaced by a prosthetic device. More particularly, the top end of the patient's femur is surgically removed, and then the lower end of the prosthetic device is secured in the intramedullary canal of the femur, e.g., by tapping and cementing. In many cases, the patient's femur may be weakened, either by age or disease or injury or surgical trauma. Accordingly, in many cases the surgeon may elect to reinforce the top end of the patient's femur by wrapping a length of surgical wire around the outside of the femur and then twisting the two free ends of the wire together so as to secure the wire in place with the desired tension. See, for example, FIG. 1, which shows several lengths of surgical wire 20 secured around the upper end of a femur 22 so as to reinforce the femur about a prosthetic device 24.

By way of another example, in a so-called "open heart" procedure, the patient's sternum is typically cut down its middle so as to permit the patient's rib cage to be spread apart and the patient's heart exposed. In many cases, at the conclusion of the surgery, the surgeon may elect to wire the sternum back together using surgical wire. In particular, the sternum is wired back together by passing a length of surgical wire across the separated sternum and then twisting the two free ends of the wire together so as to secure the wire in place with the desired tension. See, for example, FIG. 2, which shows several lengths of surgical wire 20 holding together a sternum 26.

By way of still another example, and referring now to FIG. 3, surgical wires 20 may also be used to hold a bone graft 28 in place in a spinal column 30.

Conventional surgical wires are generally of two types: (1) a single elongated solid strand of metal, such as stainless steel; and (2) a cable including a multiplicity of elongated thin strands of metal. The former construction is generally of greater tensile strength than the latter construction, and is generally less likely to give way or break down over extended periods of time. However, a surgical wire formed out of a single strand of metal is typically fairly stiff and hence difficult to guide around bone. On the other hand, while the cable construction generally provides the flexibility desired by physicians for guiding around bone, it is generally lacking in strength and more likely to fail in due course.

It is, therefore, desirable to have available surgical wire having the flexibility of the cable type and the strength of the solid strand type.

OBJECTS OF THE INVENTION

Accordingly, an object of the present invention is to provide a surgical wire having the flexibility needed to be easily guided around bone, and the strength needed to maintain retention of the bone over an extended period of time.

A further object of the present invention is to provide a method for applying surgical wire to bone.

SUMMARY OF THE INVENTION

The above and other objects of the present invention are addressed by the provision and use of a novel surgical wire assembly.

The novel surgical wire assembly includes a first portion comprising a cable including multiple elongated strands of metal, and a second portion comprising an elongated solid strand of metal, the first and second portions being joined end-to-end. The first portion is more flexible than the second portion, and the second portion is constructed so as to have a tensile strength exceeding the tensile strength of the first portion.

The objects of the present invention are further addressed by the provision and use of a novel method for applying a surgical wire to bone. The novel method comprises the step of providing a surgical wire assembly comprising first and second portions joined end-to-end. The first portion comprises a cable including multiple elongated strands of metal, and the second portion comprises an elongated solid strand of metal, the first portion being more flexible than the second portion, and the second portion having a tensile strength greater than the tensile strength of the first portion.

In one preferred form of the present invention, the novel method further comprises the steps of positioning a wire passer around bone; inserting an end of the first portion of the surgical wire assembly into an end of the wire passer; moving the first portion of the surgical wire assembly through a head portion of the wire passer and out a conduit proximate the head portion; pulling the first portion of the surgical wire assembly through the wire passer until the second portion of the surgical wire assembly is in the wire passer and extends around the bone; removing the wire passer from the surgical wire assembly; and connecting together first and second segments of the second portion of the surgical wire assembly, such that the second portion of the surgical wire assembly encircles and is bound around the bone.

BRIEF DESCRIPTION OF THE DRAWINGS

The above and other objects and features of the present invention will be more fully disclosed or rendered obvious by the following detailed description of the preferred embodiments of the invention, which description is to be considered together with the accompanying drawings wherein like numbers refer to like parts, and further wherein.

DETAILED DESCRIPTION OF THE PREFERRED EMBODIMENTS

Figure 1:
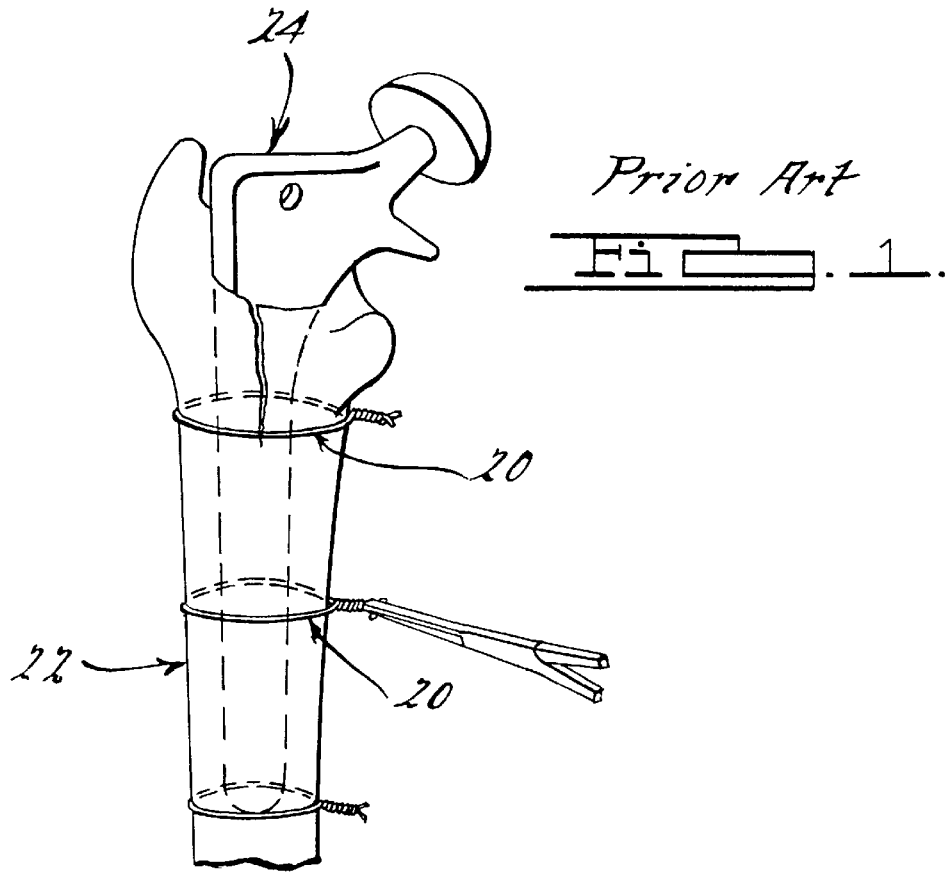
FIG. 1 is a perspective view showing lengths of surgical wire encircling a top portion of a human femur, as is known in the art.
Figure 2:
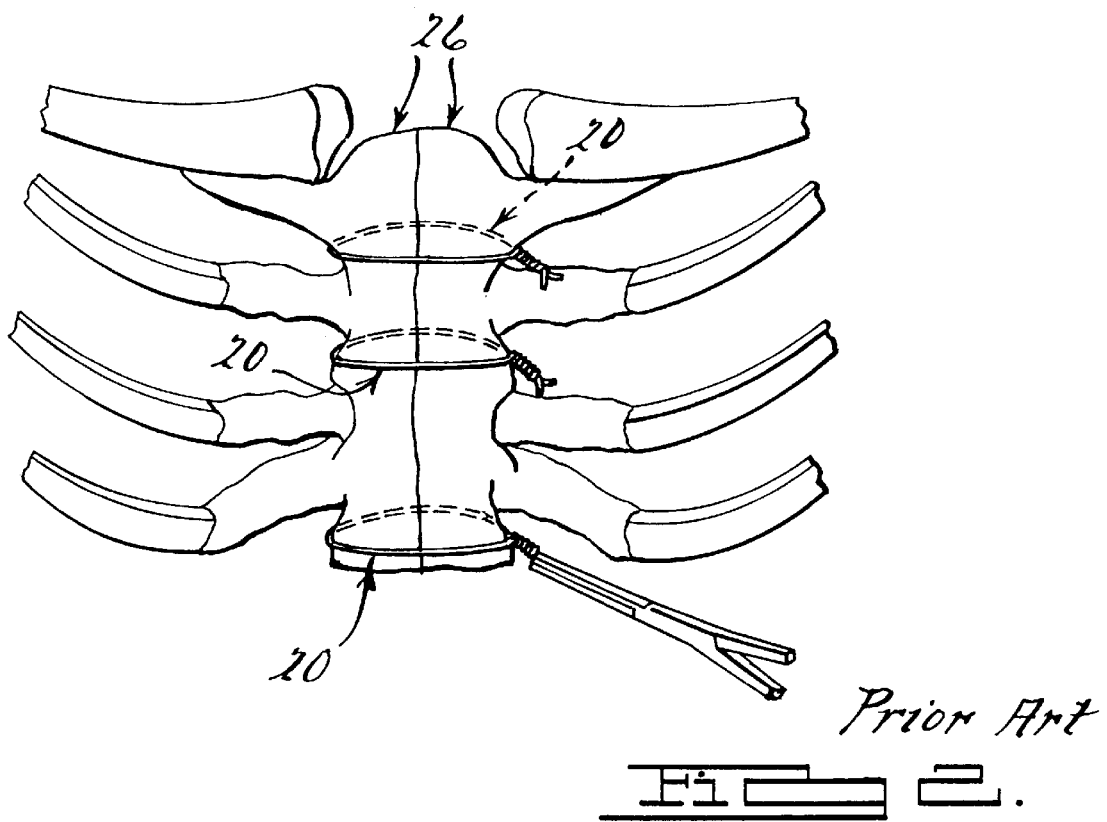
FIG. 2 is a perspective view showing lengths of surgical wire encircling a human sternum, as is known in the art.
Figure 3:
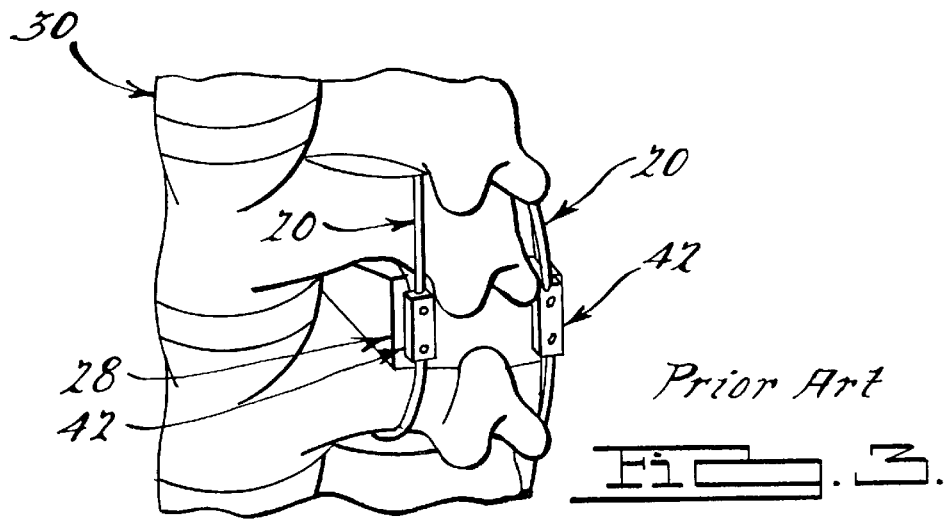
FIG. 3 is a perspective view showing surgical wire retaining a bone graft in place in a spinal column, as is known in the art.
Figure 4:
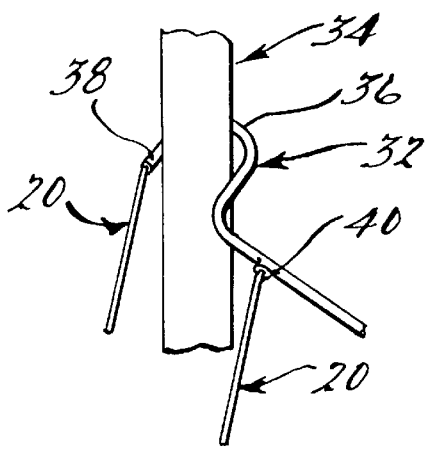
FIG. 4 is a perspective view showing a wire passer disposed for passing wire around a bone, as is known in the art.
Figure 5:
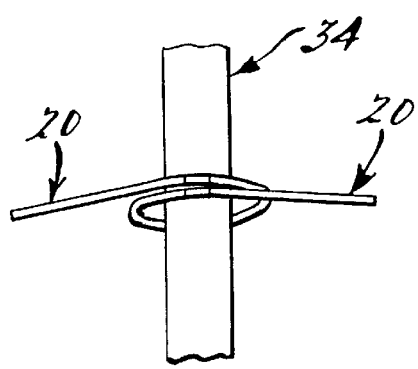
FIG. 5 is a perspective view showing surgical wire encircling the bone, with the wire passer having been removed, as is known in the art.
Figure 6:
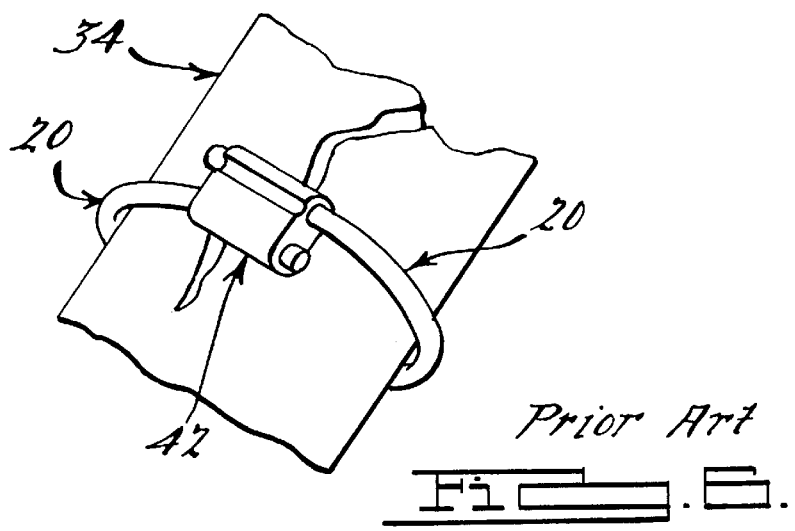
FIG. 6 is an enlarged perspective view showing one means for binding the surgical wire to the bone, as is known in the art.

Referring now to FIG. 4, it will be seen that a tool 32, commonly referred to as a "wire passer", may be used to guide the wire 20 around a bone 34. Wire passer 32 generally includes a hollow head portion 36 which is configured and sized so as to be passed around bone 34 and to be disposed in close proximity to bone 34. The cable 20, or solid wire 20, which is to be wrapped around bone 34 is introduced into a distal end 38 of the wire passer's head portion 36 and is pushed through head portion 36 and out through a hollow conduit 40. Once wire 20 is in place around bone 34, wire passer 32 is removed, leaving the cable 20, or solid wire 20, wrapped around bone 34 (FIG. 5). The cable 20, or wire 20, may then be twisted together, as shown in FIGS. 1 and 2, or clamped in a grip 42, as shown in FIGS. 3 and 6.

Due to the inherent stiffness of solid wire, a surgical wire 20 which is formed out of a single elongated solid strand of metal is generally fairly difficult to push through the curved wire passer. As noted above, cables are more flexible than solid wires of the same size, but such cables usually lack the strength of solid wire, which strength is desirable in bone wiring applications.

Figure 7:
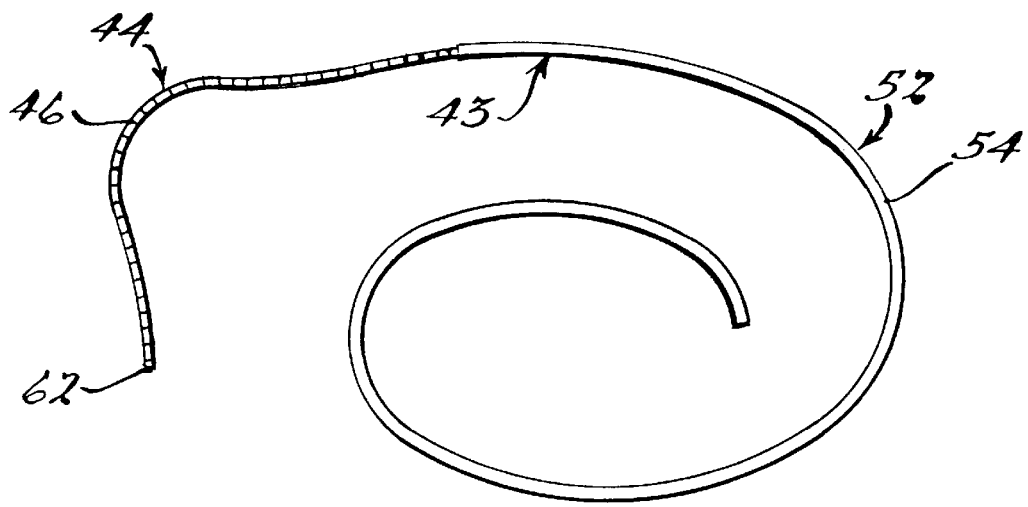
FIG. 7 is an interrupted side elevational view of a novel surgical wire assembly formed in accordance with the present invention.
Figure 9:
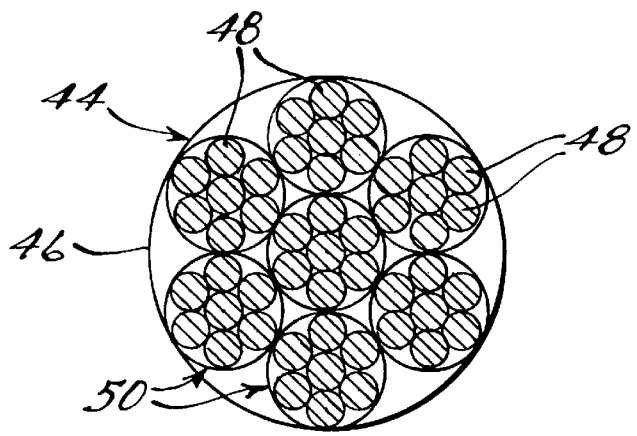
FIG. 9 is a sectional view taken along line 9—9 of FIG. 8.

Referring next to FIG. 7, a novel surgical wire assembly 43 is shown which is formed in accordance with the present invention. Surgical wire assembly 43 comprises a first portion 44 comprising a cable 46 including multiple strands 48 (FIG. 9), preferably of metal. In the embodiment shown in FIG. 9, cable 46 includes seven bundles 50 of strands 48, each bundle 50 including seven strands 48. As is well known in the cable art, there are many different variations of cable construction, and no particular structure of cable is believed to be critical to the present invention. The cable 46 is preferably provided with a diameter of about 0.9–2.0 mm.

The strands 48, or individual wires, within cable 46, are preferably made of stainless steel; or cobalt chrome; or titanium; or an alloy of titanium; or an alloy of chrome, chromald, nickel and vanadium; or an alloy of titanium, aluminum and vanadium; but may also be made of any suitable material providing the requisite flexibility, strength, biocompatibility, and susceptibility to sterilization.

Surgical wire assembly 43 further includes a second portion 52 comprising an elongated solid strand 54 of metal, such as stainless steel.

Figure 8:
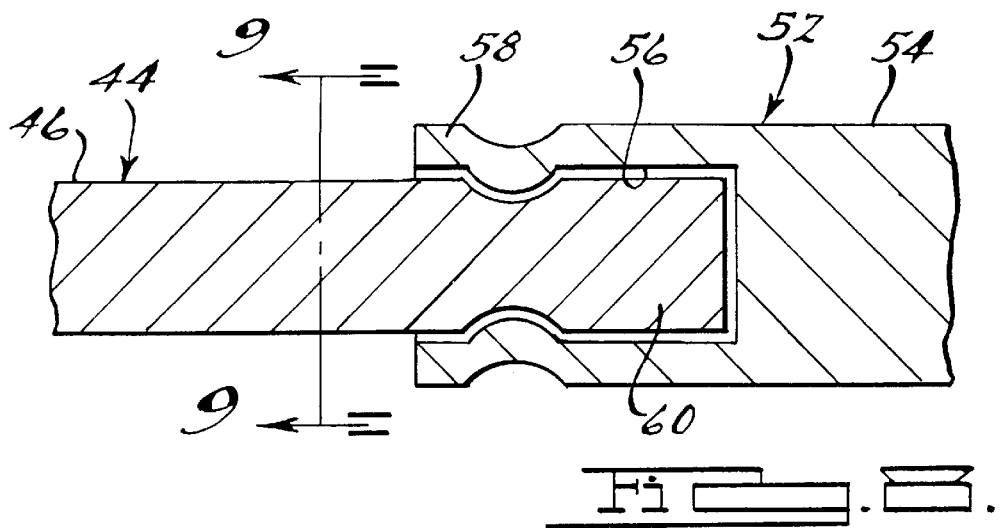
FIG. 8 is a centerline sectional view of end portions of the surgical wire assembly of FIG. 7, showing the end portions crimped together.
Figure 10:
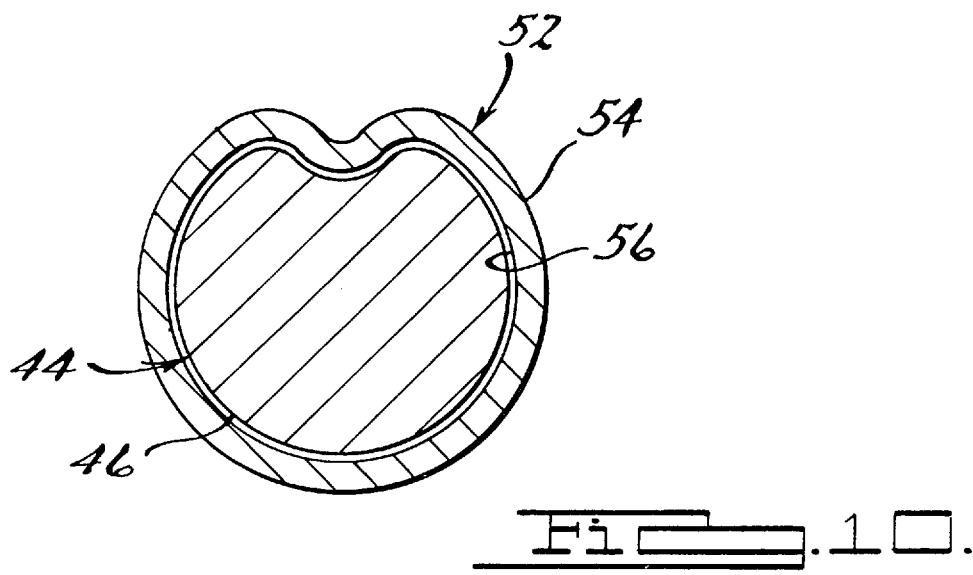
FIG. 10 is a transverse sectional view of the crimped end portion of FIG. 8.
Figure 11:
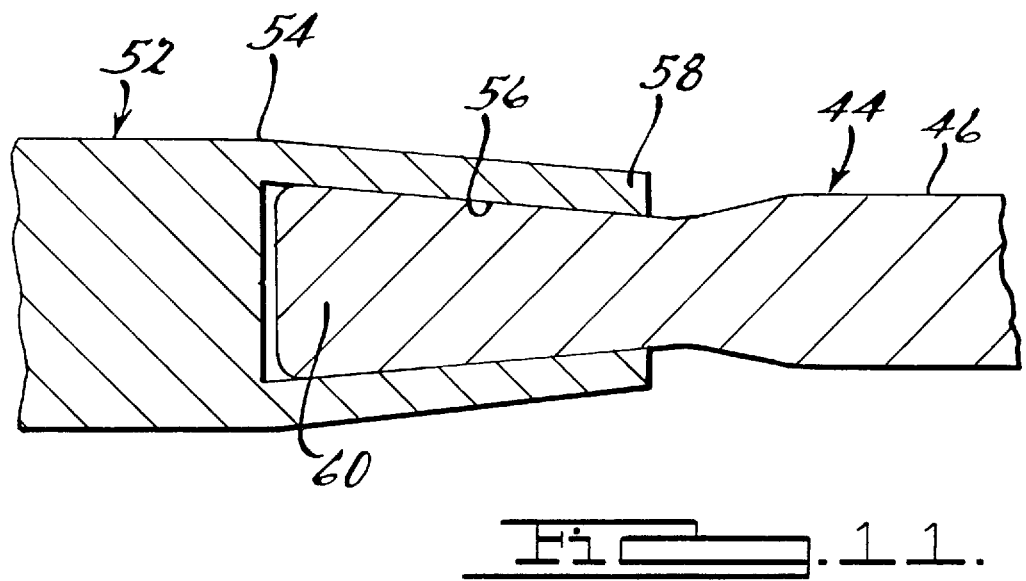
FIG. 11 is similar to FIG. 8, but showing the end portions swaged together.
Figure 12:
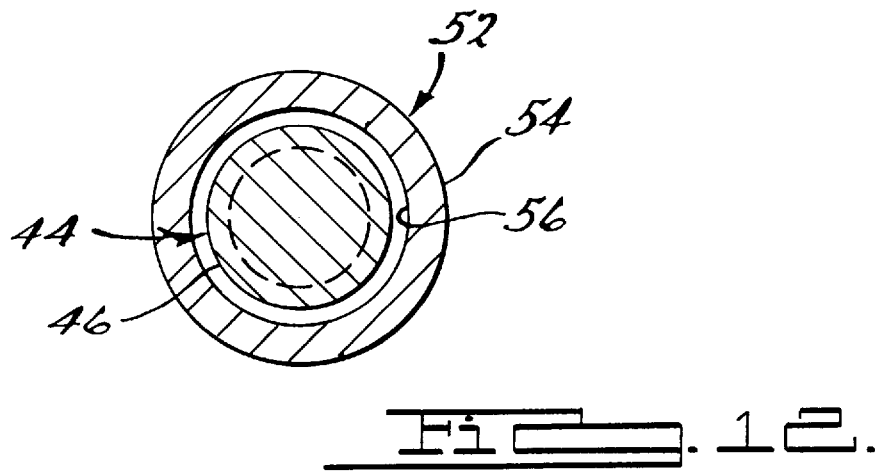
FIG. 12 is a transverse sectional view of the crimped end portion of FIG. 11.

The first and second portions 44, 52 are joined together (FIG. 8) in an end-to-end fashion. In preferred embodiments, illustrated in FIGS. 8 and 11, the solid strand of metal 54 is provided with a slightly larger diameter than the cable 46, and an end 58 of metal strand 54 is provided with an axial bore 56 for receiving an end 60 of cable 46. The cable 46 is made fast to solid metal strand 54 by crimping (FIGS. 8 and 10) or swaging (FIGS. 11 and 12).

In one preferred use of the above-described surgical wire assembly 43, a physician first positions wire passer 32 (FIG. 4) around bone 34 and between bone 34 and surrounding tissue (not shown). Then a free end 62 (FIG. 7) of the surgical wire assembly's first portion 44 is inserted into end 38 of wire passer 32 and pushed through head portion 36 of wire passer 32 and out through conduit 40. In this respect it will be appreciated that the flexible nature of first portion 44, which is formed with a cable-type construction, will permit the leading end of the surgical wire assembly to be easily threaded through wire passer 32.

Grasping free end 62 of the wire assembly's first portion 44, the operator then pulls cable 46 through the wire passer's head portion 36 until metal strand 54 is in wire passer 32 and extends around bone 34. Next, while holding surgical wire assembly 43 in place, the wire passer 32 is removed, leaving wire assembly 43 encircling the bone. The solid strand 54 of surgical wire assembly 43 is then twisted, or clamped, or otherwise joined together, such that the solid strand 54 is bound around bone 34. The superfluous ends of strand 54, and all of cable 46, may then be snipped off, leaving only the solid wire 54 disposed at the bone site.

It will, of course, be appreciated that numerous modifications may be made to the preferred embodiments discussed above, and/or their method of use, without departing from the scope of the present invention.

For example, it will be apparent to those skilled in the art that the aforementioned first and second portions 44, 52 may be connected together end-to-end by any suitable means other than crimping and swaging.

Furthermore, it is possible to deploy the novel surgical wire assembly around bone by using means other than a wire passer of the sort discussed above. By way of example, forceps may be used to pass the surgical wire assembly around bone.

It is also possible to form a novel surgical wire assembly wherein first portions 44 may be disposed on either end of a second portion 52, so as to make a surgical wire serially comprising a first portion 44, a second portion 52, and then another first portion 44.

Still other changes will be apparent to a person skilled in the art in view of the foregoing disclosure. Accordingly, it is to be understood that the present invention is by no means limited to the particular constructions and steps herein disclosed and/or shown in the drawings, but also comprises any modification or equivalents within the scope of the claims.

Thus there is provided a novel surgical wire assembly having the flexibility needed to be easily pushed through a wire passer, and having the strength needed to provide long-term retention of bone and/or bone parts. There is further provided a method for applying surgical wire to one or more bones or bone parts, utilizing the novel surgical wire assembly disclosed herein.

What is claimed is:

1. A surgical wire assembly comprising:
   a first portion comprising a cable including multiple elongated strands of metal; and
   a second portion comprising an elongated solid strand of metal;
   said first and second portions being joined end-to-end;
   said first portion being more flexible than said second portion; and
   said second portion having a tensile strength exceeding the tensile strength of said first portion, wherein said first portion is provided with a diameter of about 0.9–2.0 mm, and said second portion is provided with a diameter greater than said diameter of said first portion.

2. A surgical wire assembly according to claim 1 wherein said strands of said cables are each of a material selected from a group of materials consisting of stainless steel; cobalt chrome; titanium; an alloy of titanium; an alloy of chrome, chromald, nickel and vanadium; and an alloy of titanium, aluminum and vanadium.

3. A surgical wire assembly according to claim 2 wherein said solid strand of metal is of stainless steel.

4. A surgical wire assembly according to claim 1 wherein said end of said second portion is provided with an axial bore, and said end of said first portion is fixed in said bore.

5. A surgical wire assembly according to claim 4 wherein said first portion end is fixed in said second portion bore by deformation of said second portion.

6. A surgical wire assembly according to claim 5 wherein said deformation comprises portions of said second portion extending inwardly into said first portion.

7. A surgical wire assembly according to claim 6 wherein said deformation comprises a crimp.

8. A surgical wire assembly according to claim 6 wherein said deformation comprises a swaged portion of said second portion.

9. A surgical wire assembly according to claim 1 wherein said assembly comprises, in serial fashion, a first portion, a second portion, and another first portion.

10. A method for applying a surgical wire assembly to a bone, the method comprising the steps of:
    providing a surgical wire assembly comprising first and second portions joined end-to-end, said first portion comprising a cable including multiple elongated strands of metal, and said second portion comprising an elongated solid strand of metal, said first portion being more flexible than said second portion, and said second portion having a tensile strength greater than the tensile strength of said first portion;
    positioning said surgical wire assembly around the bone, by passing said first portion of said surgical wire assembly around the bone and then pulling on said first portion until the second portion of said surgical wire assembly is brought around the bone; and
    connecting together first and second segments of the second portion of said surgical wire assembly, such that said second portion of said surgical wire assembly encircles and is bound around the bone.

11. A method for applying a surgical wire assembly to a bone, the method comprising the steps of:
    providing a surgical wire assembly comprising first and second portions joined end-to-end, said first portion comprising a cable including multiple elongated strands of metal, and said second portion comprising an elongated solid strand of metal, said first portion being more flexible than said second portion, and said second portion having a tensile strength greater than the tensile strength of said first portion;
    positioning a wire passer around the bone;
    inserting an end of said first portion of the surgical wire assembly into an end of said wire passer;
    moving said surgical wire assembly through a head portion of said wire passer and out a conduit proximate said head portion;
    pulling said first portion of said surgical wire assembly through said wire passer until said second portion is in said wire passer and around the bone;
    removing said wire passer from said surgical wire assembly; and
    connecting together first and second segments of said second portion of said surgical wire assembly, such that said second portion of said surgical wire assembly encircles and is bound around the bone.

12. A method according to claim 11 including the further step of snipping off elements of said second portion of said surgical wire assembly not encircling said bone and all of said first portion of said surgical wire assembly.

13. A method for applying a surgical wire assembly to a bone, said method comprising:
    providing a surgical wire assembly having at least a first portion formed from a cable having multiple elongated strands of metal and a second portion formed from an elongated solid strand of metal with said first and second portions joined end-to-end;
    positioning said surgical wire assembly around at least a portion of the bone by passing said first portion of said surgical wire assembly around at least the portion of the bone and then pulling on said first portion until said second portion of said surgical wire assembly is brought around at least the portion of the bone; and
    connecting together first and second segments of said second portion of said surgical wire assembly, whereby said second portion of said surgical wire assembly encircles and is bound around at least the portion of the bone.

14. The method as defined in claim 13 wherein said first portion of said surgical wire assembly is more flexible than said second portion of said surgical wire assembly.

15. The method as defined in claim 13 wherein said second portion of said surgical wire assembly has a tensile strength greater than a tensile strength of said first portion of said surgical wire assembly.

16. The method as defined in claim 13 further comprising providing a third portion of said surgical wire assembly, said third portion of said surgical wire assembly formed from a cable including multiple elongated strands of metal and being connected end-to-end with said second portion of said surgical wire assembly.

17. The method as defined in claim 13 further comprising:
    positioning a wire passer around the bone;
    inserting an end of said first portion of said surgical wire assembly into an end of said wire passer;
    pulling said first portion of said surgical wire assembly through said wire passer until said second portion is in said wire passer and around at least a portion of the bone; and
    removing said wire passer from said surgical wire assembly.

* * * * *